United States Patent [19]

Walsh et al.

[11] Patent Number: 5,025,920
[45] Date of Patent: Jun. 25, 1991

[54] EVIDENCE GATHERING KIT

[76] Inventors: Alison J. Walsh, 34 High St., Sharon, Mass. 02067; Jean T. Walsh, 162-21 Powells Cove Blvd., Beechhurst, N.Y. 11357

[21] Appl. No.: 581,574
[22] Filed: Sep. 11, 1990
[51] Int. Cl.⁵ .......................................... B65D 85/00
[52] U.S. Cl. .................................. 206/223; 206/456
[58] Field of Search .............. 206/223, 229, 361, 362, 206/363, 370, 454, 456, 569, 570

[56] References Cited

U.S. PATENT DOCUMENTS

| | | |
|---|---|---|
| 1,644,830 | 2/1924 | Henderson . |
| 1,910,236 | 5/1929 | Butler . |
| 2,013,281 | 9/1935 | McCalla .............................. 206/456 |
| 2,410,928 | 6/1944 | Christner et al. . |
| 2,738,872 | 3/1956 | De Boton ........................... 206/456 |
| 2,790,547 | 4/1957 | Sutton ................................ 206/456 |
| 2,835,246 | 12/1954 | Boettger .............................. 128/2 |
| 3,203,540 | 12/1962 | Kalt et al. . |
| 3,272,319 | 10/1962 | Brewer . |
| 3,913,562 | 10/1975 | Moore et al. ...................... 128/2 W |
| 3,917,456 | 11/1975 | Eckstein et al. ................... 23/254 R |
| 3,935,944 | 2/1976 | Wilson et al. ....................... 206/223 |
| 4,078,656 | 3/1978 | Crane et al. ......................... 206/223 |
| 4,128,173 | 12/1978 | Lazarus et al. ..................... 206/570 |
| 4,175,439 | 11/1979 | Laker ................................ 73/425.4 R |
| 4,195,059 | 3/1980 | Whitcher et al. ................... 422/61 |
| 4,311,792 | 1/1982 | Avery ................................... 435/30 |
| 4,327,744 | 5/1982 | Smith ................................... 128/759 |
| 4,595,102 | 6/1986 | Cianci et al. ........................ 206/572 |
| 4,803,048 | 2/1989 | Nason ................................... 206/569 |

FOREIGN PATENT DOCUMENTS 8702803  5/1987  PCT Int'l Appl. ................ 206/456

Primary Examiner—Jimmy G. Goster

[57] ABSTRACT

An evidence gathering kit for gathering and handling body and body fluid evidence. The kit is comprised of a covered, compartmentalized cardboard storage box with applicators, swabs, wipes, unbreakable slides, porous bags and paper envelopes. The kit also contains a Styrofoam slide holder.

11 Claims, 5 Drawing Sheets

EVIDENCE GATHERING KIT

BACKGROUND OF THE INVENTION

The present invention relates to evidence gathering kits, and more particularly to improvements therein for gathering and handling body and body fluid evidence.

Body and body fluid evidence, i.e., blood, semen, saliva, urine, DNA samples, hair samples, etc., for certain types of crimes, e.g., rape, are critical for the determination of likely suspects and for proving the guilt or innocence of an accused at trial. The time span between the crime's incidence and later investigation and/or trial can be lengthy. Body fluid evidence is especially subject to destruction, compromise, deterioration, and/or contamination because of aging, humidity, improper and/or rough handling. Body fluid specimens will deteriorate because of humidity and age. Specimen slides will break due to rough handling. Slide breakage and/or the jostling together of various applicators, swabs and wipes may cause contamination of individual specimens. Various evidence specimens can become separated due to improper handling thereby compromising the evidence.

It is desirable to have a kit which permits gathering and storing of body and body fluid evidence in a convenient manner and yet in a manner which facilitates proper evidence handling. The kit should also lend itself to keeping the specimens dry and be easily refrigerated. In the past, storage boxes with slides, applicators, swabs, bags, envelopes, and other evidence gathering paraphernalia loosely assembled therein have been used. However, this configuration lends itself to contamination among samples, breakage due to rough handling, and poor trackability of specimens. Plastic baggies have been commonly used to prevent contamination. However, this retards sample drying. Dry samples are less subject to deterioration than "wet" samples. All evidence specimens from a particular incident are placed together for convenience, albeit usually individually packaged, in a container. Because of the number of individuals handling the evidence during an investigation and later trial, there is much jostling together of the specimens. As a result, evidence is frequently contaminated and/or compromised.

SUMMARY OF THE INVENTION

A principal feature of the present invention is the provision of an improved evidence gathering kit for gathering and handling body and body fluid evidence.

The kit of the present invention comprises a compartmentalized storage box, and within said box several cotton applicators, several swabs, several wipes, several slides, and several paper bags.

A feature of the present invention is that the box has a compartment for the swabs and applicators, a compartment for the wipes, a holder within a compartment for the slides, and a compartment for larger bagged items.

Another feature of the invention is that the compartments and slide holder protects the specimens from breaking and/or contaminating each other.

Yet another feature of the invention is that the invention keeps humidity to a minimum by its use of paper storage bags and envelopes.

A further feature of the invention is that the entire invention is appropriate for refrigeration.

Still another feature of the invention is that all specimens are kept together in the same storage box.

These together with other objects of the invention, along with various features of novelty which characterize the invention, are pointed out with particularity in the claims annexed to and forming a part of this disclosure. For a better understanding of the invention, its operating advantages and the specific objects attained by its uses, referenced should be had to the accompanying drawings and descriptive matter in which there is illustrated a preferred embodiment of the invention.

DETAILED DESCRIPTION OF THE PREFERRED EMBODIMENT

Figure 1:
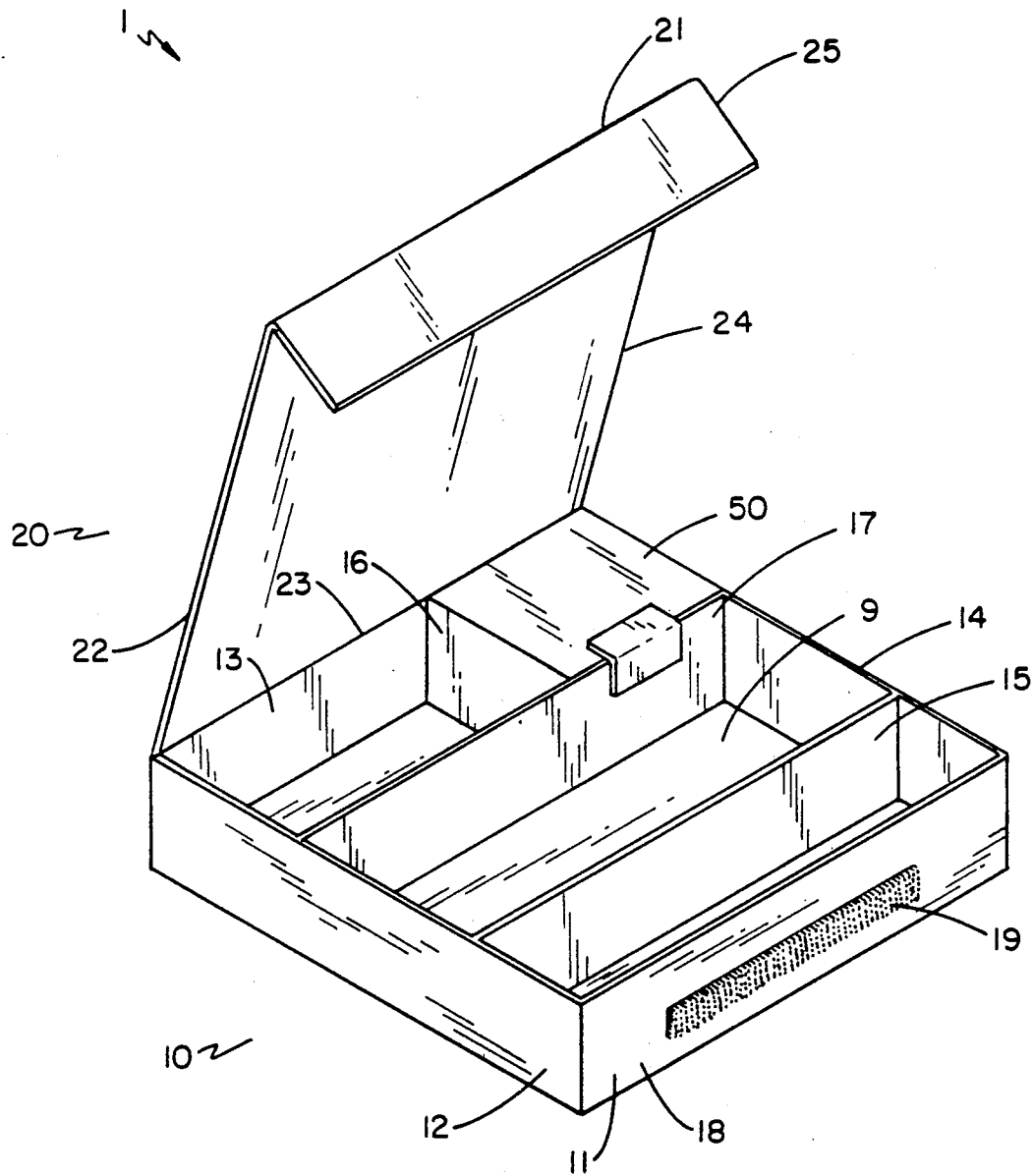
FIG. 1 is a perspective view of an evidence gathering kit according to the present invention.
Figure 2:
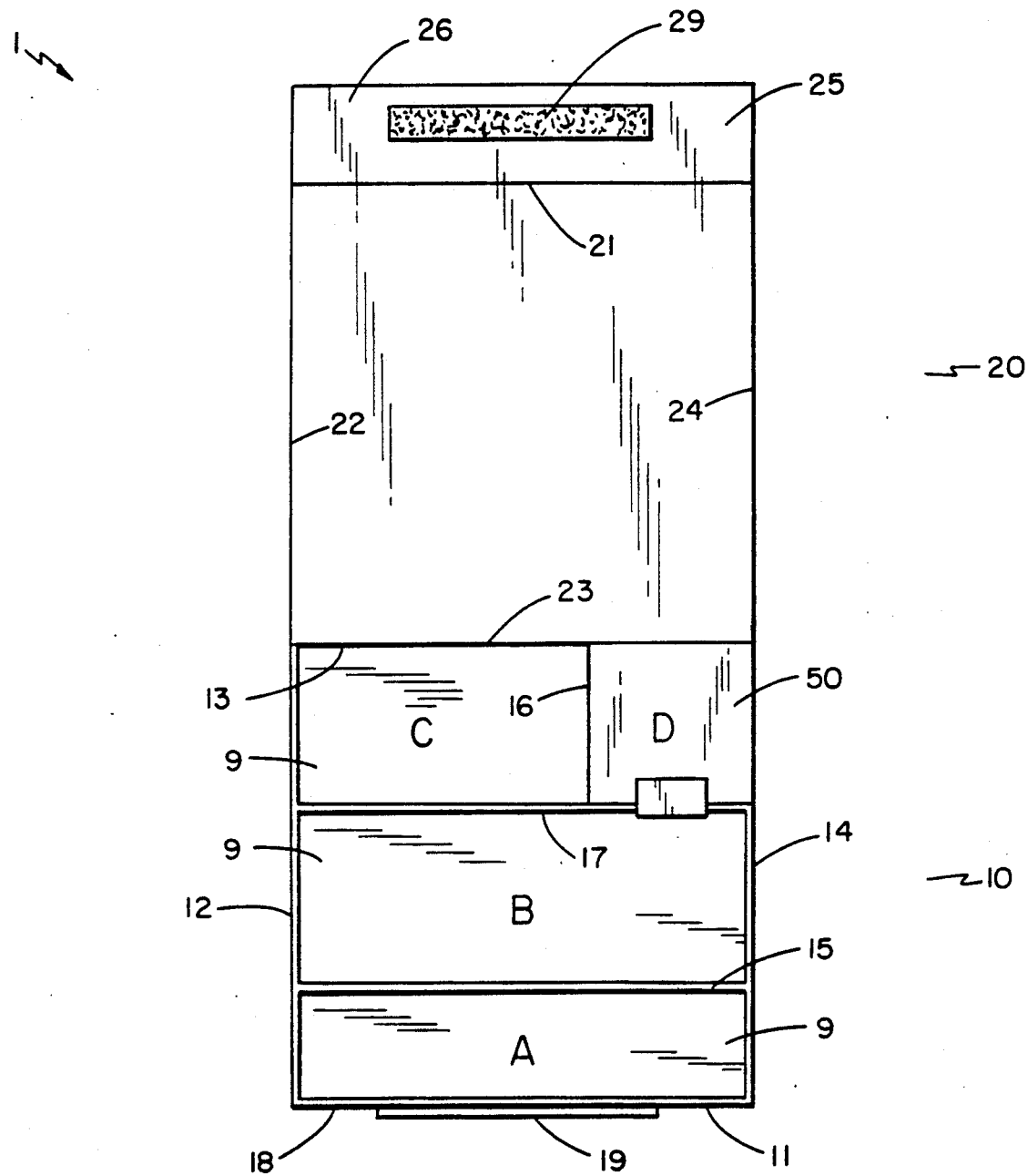
FIG. 2 is a top plan view of the kit of FIG. 1 with its cover member open.
Figure 3A:
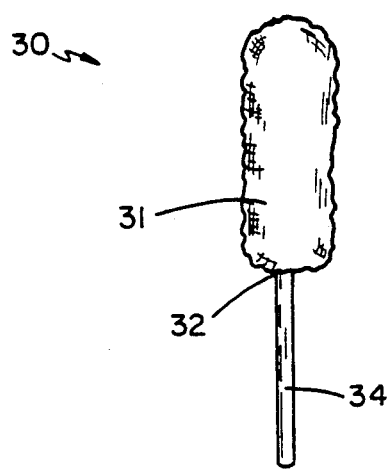
FIG. 3A is an elevational view of an applicator used in the present invention.
Figure 3B:
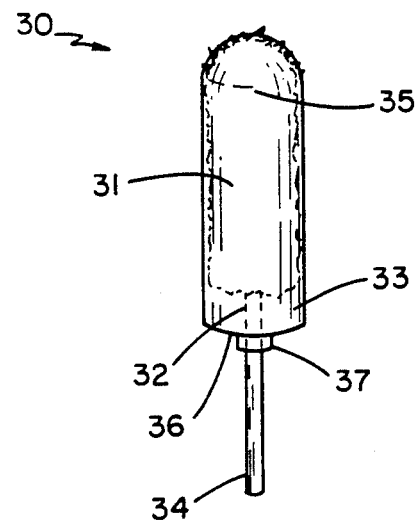
FIG. 3B is an elevational view of the applicator of FIG. 3A placed within a plastic cylinder.
Figure 3C:
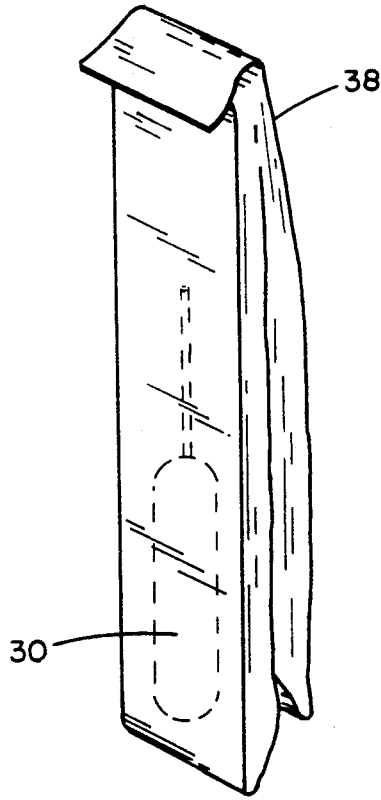
FIG. 3C is a perspective view of a bagged applicator.
Figure 3D:
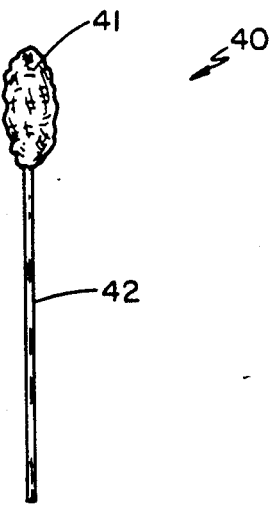
FIG. 3D is an elevational view of a swab used in the present invention.
Figure 4:
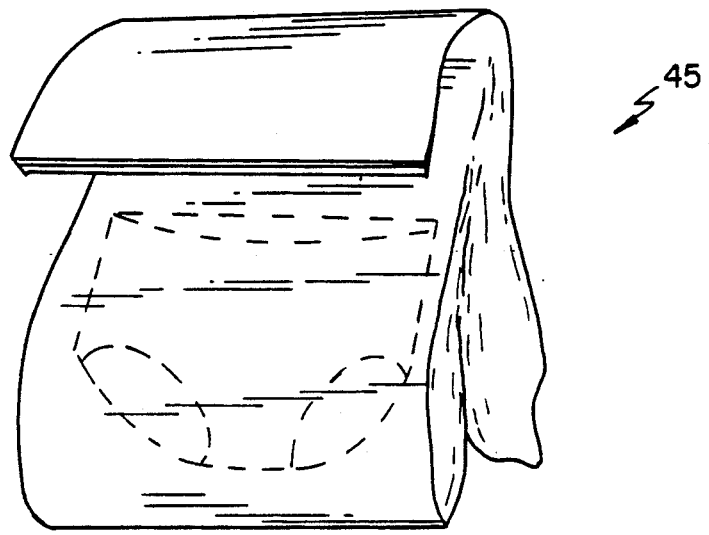
FIG. 4 is a perspective view of a bagged undergarment.
Figure 5:
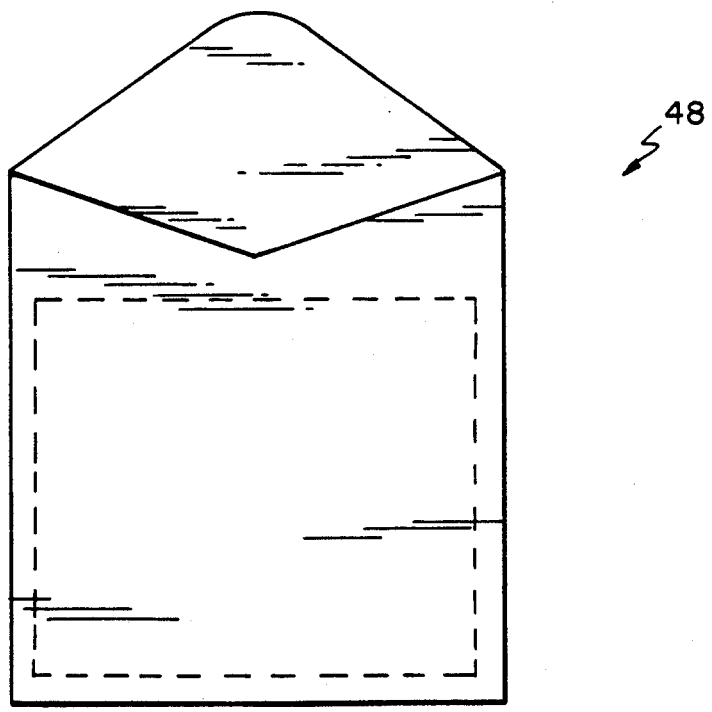
FIG. 5 is an elevational view of an evidence envelope used in the present invention.
Figure 6A:
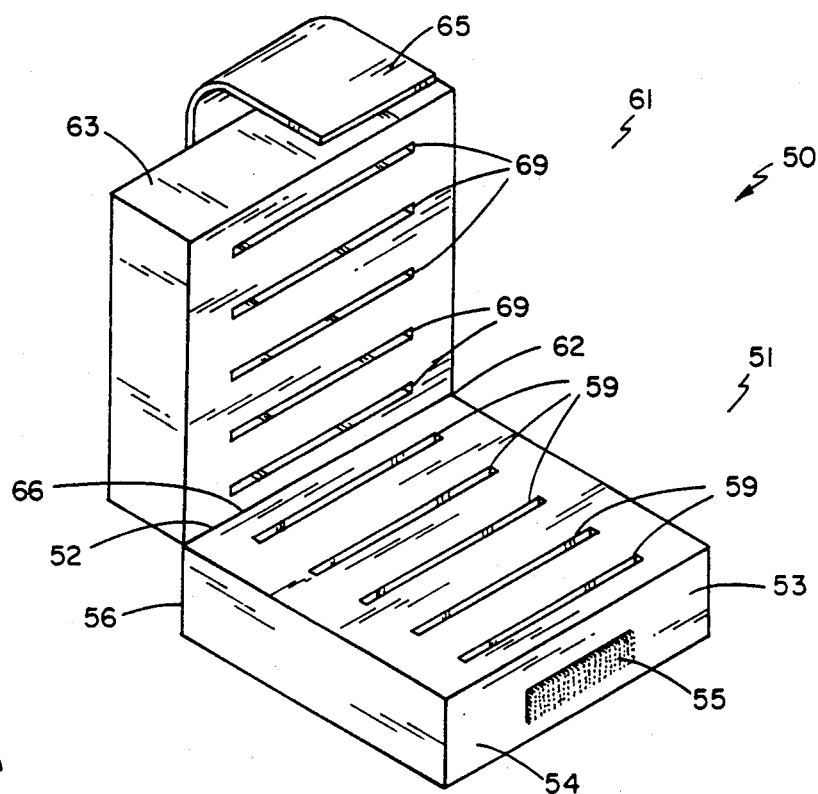
FIG. 6A is a perspective view of the slide holder used in the present invention.
Figure 6B:
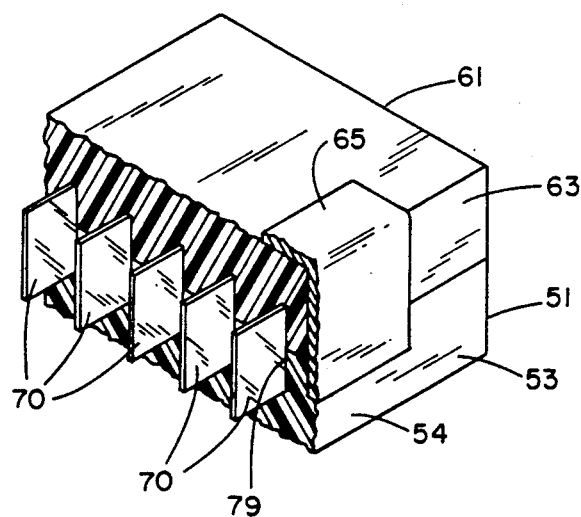
FIG. 6B is a perspective view of the slide holder in a closed position.
Figure 6C:
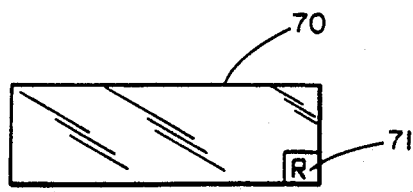
FIG. 6C is a plan view of a specimen slide used in the present invention.

Referring to the drawings in detail wherein like elements are indicated by like numerals, there is shown an evidence gathering kit incorporating the features of the present invention. Reference numeral 1 refers to the kit storage box 1. The box 1 is made out of corrugated cardboard and has a generally rectangular base member 10 and a corresponding cover member 20. The base member 10 is comprised of substantially parallel front 11 and rear 13 walls, substantially parallel side walls 12 and 14, and a flat bottom 9 extending from the front 11 to rear 13 walls and from side wall 12 to side wall 14. The base member 10 also has two divider walls 15 and 17 parallel to the front 11 and rear 13 walls extending from one side wall 12 to the other 14. The rearward divider wall 17 has a small divider wall 16 extending rearward to the rear wall 13 substantially parallel to the side walls 12 and 14. The base member walls 11-17 form four compartments A, B, C and D. Other divider walls may be added or subtracted to increase or decrease the number of compartments formed thereby. The base member front 11 and rear 13 walls are approximately five inches long and two inches high. The base member side walls 12 and 14 are approximately eight inches long and two inches high.

The cover member 20 is generally flat and has four edges 22, 24, 21, and 23 which correspond to the base member sides 12 and 14, front 11 and rear 13 walls. The cover member rear edge 23 is pivotally hinged along its length to the top edge of the base member rear wall 13. The cover member front edge 21 terminates in a downwardly extending flap 25 with a Velcro strip 29 on the flap's inner face 26. A corresponding Velcro strip 19 is positioned along the base member front wall outer face 18. When the cover member flap 25 is pressed against the base member front wall outer face 18, both Velcro strips 19 and 29 interlock.

Compartment A holds the invention's applicators 30 and swabs 40 both before and after use. Compartment B holds bagged items 45 such as underwear. Compartment C holds wipes before and after use as well as other items of evidence. Compartment D holds a slide holder 50 and slides 70.

The invention applicators 30 are each comprised of a compressed cotton cylinder 31 with a flexible plastic or paper rod 34 concentrically positioned within the cotton cylinder 31 along the cylinder's longitudinal axis and extending out of one end 32 of the cotton cylinder 31. The applicator 30 is used for vaginal and rectal smears. A plastic cylinder 33 is positioned over the cotton cylinder 31 to facilitate entry of the applicator 30 into vaginal or rectal openings. The plastic cylinder 33 is contoured at its forward end 35 for ease of entry. Its rearward end 36 has an opening through which the applicator rod 34 extends. After use, the applicator 30 is placed into an elongated paper bag 38 and sealed. The bag 38 is marked as to what part of the body the specimen was taken, who it was taken from, who took the specimen, and the date. It is important that the bag 38 be porous to allow drying. For this reason, a plastic bag would be a poor choice of materials. The marked bag 38 with applicator 30 contained therein is then placed into compartment A.

The invention swabs 40 are comprised of compressed cotton ovals 41 attached to the end of a rod 42. The swabs 40 are used for oral specimens and for other body openings to supplement the applicators or where an applicator 30 would not be readily convenient. The swab 40 is placed into an elongated paper bag 38 after use and sealed. The bag 38 is also marked as to what body part the specimen was taken from, who it was taken from, who took the specimen, and the date the specimen was taken. The bagged swab 40 is also stored in compartment A. The elongated shape of compartment A is especially convenient for storing the elongated bags 38 containing applicator 30 and swab 40 specimens. The bagged applicators 30 and swabs 40 resting against each other minimize jostling and are isolated from specimens and evidence in the other compartments.

Compartment B is used for holding larger items of evidence such as bagged undergarments 45. Compartment C is used for holding wipes, fingernail scrapings, head and pubic hair samples. The wipes are gauze or compressed cotton pads used for externally swabbing all body areas. Each used wipe is placed into a paper envelope 48, sealed and marked in the same manner as the applicator and swab bags 38. Head and pubic hair samples are often obtained and would also be placed into separate envelopes 48 marked "pubic" hair combings and "head" combings, sealed and marked in same manner as the other specimen bags 38 and envelopes 48. Fingernail scrapings are placed into separate paper envelopes 48, labeled "right Hand" or "left Hand", sealed and marked according to the procedures described above for other specimens. The envelopes 48 are placed into compartment C, one on top of the other. As with the applicator and swab bags 38, the arrangement of envelopes 48, resting on one another, considerably reduces jostling and isolates the envelopes 48 from the specimens in the other compartments.

Compartment D contains a slide holder 50 and generally rectangular slides 70. The slide holder 50 is comprised of two molded, generally square, Styrofoam pieces, a base piece 51 and a cover piece 61. The pieces 51 and 61 are approximately the same size and are hinged together along each's back side edge 52 and 62, so that the cover piece 61 may be closed over the base piece 51. The base piece front side 53 has a Velcro strip 55 attached along its outside 54. The cover piece top front 63 has a Velcro tab 65. When the cover piece 61 is closed over the base piece 51, the Velcro tab 65 is pressed against the base piece Velcro strip 55, thereby interlocking both. The base 51 and cover 61 pieces have vertical, elongated, corresponding cavities 59 and 69 positioned in parallel with their front 53, 63 and rear 56, 66 sides. The cavities 59 and 69 are so arranged that when the cover 61 and base 51 pieces are joined together, the corresponding cavities 69 and 59 form enclosed chambers 79 within the holder 50.

Specimen slides 70 are held within the chambers 79. The dimensions of the chambers 79 closely match the dimensions of the slides 70, thereby providing cushioning and preventing slide 70 movement during kit handling. The slides 70 are also completely isolated from each other and from specimens in other compartments. The slides 70 themselves are made of Plexiglas or well polished plastic. This prevents breakage if a slide 70 is dropped or otherwise subject to rough handling. One corner 71 of each slide 70 has a painted surface so that a pen or marker can be used to indicate what body area corresponds to the sample on the slide 70.

While in the foregoing an embodiment of the invention has been disclosed in considerably detail for purposes of illustration, it will be understood by those skilled in the ark that many of these details may be varied without departing from the spirit and scope of the invention.

We claim:

1. An evidence gathering kit for gathering and handling body and body fluid evidence, comprising:
   a covered box with a plurality of compartments;
   a plurality of applications and swabs contained within one of said compartments;
   a plurality of elongated porous bags for enclosing individual applicators and swabs;
   a plurality of wipes contained within another of said compartments;
   a plurality of envelopes for enclosing individual wipes and other body evidence;
   a slide holder contained within another of said compartments; and
   a plurality of slides contained within said slide holder.

2. An evidence gathering kit as recited in claim 1 wherein said box is comprised of:
   a generally rectangular base member having substantially parallel front and rear walls, substantially parallel side walls, a flat bottom extending from front wall to rear wall and from side wall to side wall, forward and rearward divider walls parallel to said front and rear walls extending from one side wall to the other side wall, and a small divider wall extending from said rearward divider wall to said rear wall, wherein said walls form a plurality of compartments; and
   a corresponding, generally flat, cover member having four edges which correspond to the base member side, front and rear walls, wherein the cover rear edge is pivotally hinged along its length to the top of the base member rear wall.

3. An evidence gathering kit as recited in claim 2 wherein:
said cover member front edge terminates in a downwardly extending flap with fastening means for attachment to fastening means on the exterior of the base member front wall.

4. An evidence gathering kit as recited in claim 3 wherein:
said box is made out of cardboard.

5. An evidence gathering kit as recited in claim 4 wherein said slide holder is comprised of:
a molded, generally square, base piece having a plurality of vertical, elongated cavities; and
a molded, generally square, corresponding cover piece hinged along one edge to said base piece and having a plurality of vertical, elongated cavities corresponding to the base piece cavities;
wherein the cavities in each piece form enclosed chambers when closed for holding said slides.

6. An evidence gathering kit as recited in claim 5 wherein:
said cover piece has fastening means for attachment to fastening means on said base piece.

7. An evidence gathering kit as recited in claim 6 wherein:
said slide holder is made of Styrofoam.

8. An evidence gathering kit as recited in claim 7 wherein:
each of said slides is generally rectangular and has one corner treated to accept markings from a writing instrument.

9. An evidence gathering kit as recited in claim 8 wherein:
each of said slides is made of Plexiglas or well polished plastic.

10. An evidence gathering kit as recited in claim 9 wherein each of said applicators is comprised of:
a compressed cotton cylinder with two ends;
a flexible rod concentrically positioned within said cotton cylinder along the cylinder's longitudinal axis and extending out of one end of said cotton cylinder; and
a plastic, contoured cylinder, with two open ends, positioned over said cotton cylinder to facilitate entry of said applicator into a body opening.

11. An evidence gathering kit as recited in claim 10 wherein:
each of said swabs is comprised of a compressed cotton oval attached to the end of a rod.

* * * * *